(12) United States Patent
McVey et al.

(10) Patent No.: US 8,775,877 B2
(45) Date of Patent: Jul. 8, 2014

(54) DYNAMIC LINK LIBRARY INTEGRITY CHECKING FOR HANDHELD MEDICAL DEVICES

(75) Inventors: Gordon L. McVey, Martinsville, IN (US); Marshall M. Parker, Indianapolis, IN (US); Richard W. Wilson, Fortville, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 232 days.

(21) Appl. No.: 13/338,387

(22) Filed: Dec. 28, 2011

(65) Prior Publication Data
US 2013/0173968 A1 Jul. 4, 2013

(51) Int. Cl.
*G06F 11/00* (2006.01)
(52) U.S. Cl.
USPC .............................. 714/49; 714/758
(58) Field of Classification Search
USPC .................... 714/49, 50, 51, 52, 754, 758
See application file for complete search history.

(56) References Cited

U.S. PATENT DOCUMENTS

| 5,991,774 A * | 11/1999 | Tate et al. ............... 707/697 |
| 7,069,594 B1 | 6/2006 | Bolin |
| 7,313,824 B1 | 12/2007 | Bala et al. |
| 8,103,878 B2 | 1/2012 | Kawamae |
| 2006/0036874 A1 * | 2/2006 | Cockerille et al. ............ 713/187 |
| 2011/0072506 A1 * | 3/2011 | Law et al. ..................... 726/11 |

FOREIGN PATENT DOCUMENTS

WO WO98/33106 7/1998

\* cited by examiner

*Primary Examiner* — Dieu-Minh Le
(74) *Attorney, Agent, or Firm* — Harness, Dickey

(57) ABSTRACT

A method of checking the integrity of a dynamic link library (DLL) file called by an application being executed on a handheld medical device is described. The method includes loading a DLL from a read only memory (ROM) to a random access memory (RAM) beginning at a fixed location in the RAM. The DLL includes a first routine for performing a safety critical function of the handheld medical device and a second routine for performing a cyclical redundancy check (CRC) once the DLL is loaded to the RAM. The method includes selectively executing the first routine from the RAM. The method includes selectively executing the second routine from the RAM including: calculating a check value based on the DLL; comparing the check value with a predetermined check value; and indicating that an error is present when the check value is different than the predetermined check value.

25 Claims, 13 Drawing Sheets

Preferred load address is 50000000 ←─ 604

| Start | Length | Name | Class |
|---|---|---|---|
| 0001:00000000 | 00003514H | .text | CODE |
| 0002:00000000 | 00000418H | .rdata | DATA |
| 0002:00000418 | 00000014H | .idata$2 | DATA |
| 0002:0000042c | 00000014H | .idata$3 | DATA |
| 0002:00000440 | 0000003cH | .idata$4 | DATA |
| 0002:0000047c | 0000000cH | .idata$6 | DATA |
| 0002:00000490 | 00000164H | .edata | DATA |
| 0003:00000000 | 0000003cH | .idata$5 | DATA |
| 0003:00000040 | 00002e34H | .bss | DATA |
| 0004:00000000 | 000000d0H | .pdata | DATA |
| 0005:00000000 | 00000004H | .crc_data | DATA |
| 0006:00000000 | 00000058H | .rsrc$01 | DATA |
| 0006:00000060 | 000002a4H | .rsrc$02 | DATA |

| Address | Publics by Value | Rva+Base | |
|---|---|---|---|
| 0000:00000000 | Safe SE Handler Count | 00000000 | |
| 0000:00000000 | Safe SE Handler Table | 00000000 | |
| 0001:00000000 | Function 1 | 50001000 | |
| 0001:00000078 | Function 2 | 50001078 | |
| 0001:00000094 | Function 3 | 50001094 | |
| 0001:00000344 | Function 4 | 50001344 | |
| 0001:00000420 | Function 5 | 50001420 | |
| 0001:00000610 | Function 6 | 50001610 | 608 |
| 0001:00000908 | Function 7 | 50001908 | |
| 0001:00003058 | Function 8 | 50004058 | |
| 0001:00003290 | Function 9 | 50004290 | |
| 0001:00003318 | Function 10 | 50004318 | |
| 0001:00003368 | Function 11 | 50004368 | |
| 0001:000034f4 | Function 12 | 500044f4 | |
| 0001:00003504 | Function 13 | 50004504 | |
| 0002:00000418 | | 50005416 | |
| 0002:0000042c | | 5000542c | |
| 0003:00000000 | | 50006000 | |
| 0003:00000004 | | 50006004 | |
| 0003:00000008 | | 50006008 | |
| 0003:0000000c | | 5000600c | |
| 0003:00000010 | | 50006010 | |
| 0003:00000014 | | 50006014 | |
| 0003:00000018 | | 50006018 | 612 |
| 0003:0000001c | | 5000601c | |
| 0003:00000020 | | 50006020 | |
| 0003:00000024 | | 50006024 | |
| 0003:00000028 | | 50006028 | |
| 0003:0000002c | | 5000602c | |
| 0003:00000030 | | 50006030 | |
| 0003:00000034 | | 50006034 | |
| 0003:00000038 | | 50006038 | |
| 0005:00000000 | DLL_CRC | 5000a000 | ←─ 616 |

FIG. 6A

Preferred load address is 50000000 ← 604

| Start | Length | Name | Class |
|---|---|---|---|
| 0001:00000000 | 000034ccH | .text | CODE |
| 0002:00000000 | 0000041cH | .rdata | DATA |
| 0002:0000041c | 00000014H | .idata$2 | DATA |
| 0002:00000430 | 00000014H | .idata$3 | DATA |
| 0002:00000444 | 0000003cH | .idata$4 | DATA |
| 0002:00000480 | 0000000cH | .idata$6 | DATA |
| 0002:00000490 | 00000164H | .edata | DATA |
| 0003:00000000 | 0000003cH | .idata$5 | DATA |
| 0003:00000040 | 00002e34H | .bss | DATA |
| 0004:00000000 | 000000d0H | .pdata | DATA |
| 0005:00000000 | 00000058H | .rsrc$01 | DATA |
| 0006:00000060 | 000002a4H | .rsrc$02 | DATA |

| Address | Publics by Value | Rva+Base | |
|---|---|---|---|
| 0000:00000000 | Safe SE Handler Count | 00000000 | |
| 0000:00000000 | Safe SE Handler Table | 00000000 | |
| 0001:00000000 | Function 1 | 50001000 | |
| 0001:00000078 | Function 2 | 50001078 | |
| 0001:00000094 | Function 3 | 50001094 | |
| 0001:00000344 | Function 4 | 50001344 | |
| 0001:00000420 | Function 5 | 50001420 | |
| 0001:00000610 | Function 6 | 50001610 | 608 |
| 0001:00000908 | Function 7 | 50001908 | |
| 0001:00003008 | Function 8 | 50004008 | |
| 00001:00003240 | Function 9 | 50004240 | |
| 0001:000032d0 | Function 10 | 500042d0 | |
| 0001:00003320 | Function 11 | 50004320 | |
| 0001:000034ac | Function 12 | 500044ac | |
| 0001:000034bc | Function 13 | 500044bc | |
| 0002:00000400 | DLL_CRC | 50005400 | ← 616 |
| 0002:0000041c | | 5000541c | |
| 0002:00000430 | | 50005430 | |
| 0003:00000000 | | 50006000 | |
| 0003:00000004 | | 50006004 | |
| 0003:00000008 | | 50006008 | |
| 0003:0000000c | | 5000600c | |
| 0003:00000010 | | 50006010 | |
| 0003:00000014 | | 50006014 | |
| 0003:00000018 | | 50006018 | 612 |
| 0003:0000001c | | 5000601c | |
| 0003:00000020 | | 50006020 | |
| 0003:00000024 | | 50006024 | |
| 0003:00000028 | | 50006028 | |
| 0003:0000002c | | 5000602c | |
| 0003:00000030 | | 50006030 | |
| 0003:00000034 | | 50006034 | |
| 0003:00000038 | | 50006038 | |

FIG. 6B

DYNAMIC LINK LIBRARY INTEGRITY CHECKING FOR HANDHELD MEDICAL DEVICES

FIELD

The present disclosure relates to handheld medical devices and more particularly to data integrity checking systems and methods for handheld medical devices.

BACKGROUND

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and can be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. The incidence of diabetes is increasing rapidly, and it is estimated that between 2005 and 2030, the number of deaths from diabetes will double. In the United States, nearly 24 million Americans have diabetes with an estimated 25 percent of seniors age 60 and older being affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Management of diabetes is complex because the level of blood glucose entering the bloodstream is dynamic. Variation of insulin in the bloodstream that controls the transport of glucose out of the bloodstream also complicates diabetes management. Blood glucose levels are sensitive to diet and exercise, but also can be affected by sleep, stress, smoking, travel, illness, menses, and other psychological and lifestyle factors that are unique to each patient. The dynamic nature of blood glucose and insulin, and all other factors affecting blood glucose, often require a person with diabetes to forecast blood glucose levels. Administration of insulin and/or oral medications can be regulated and timed to maintain blood glucose levels within an appropriate range at all times.

Management of diabetes is often highly intrusive because of the need to consistently obtain reliable diagnostic information, follow prescribed therapy, and manage lifestyle on a daily basis. Diagnostic information, such blood glucose level, can be obtained from a capillary blood sample with a lancing device and a test strip. The blood glucose level is measured via the test strip using a handheld blood glucose meter. Interstitial glucose levels can be obtained from a continuous glucose sensor worn on the body.

A therapy regimen for a patient can be established based on one or more of the patient's blood glucose levels. The therapy regimen can include administration of insulin and/or oral medication. Insulin can be administered with a syringe, an insulin pen, an ambulatory infusion pump, or a combination of two or more of the above. With insulin therapy, determining the amount of insulin to inject at a given time can require forecasting meal amount and composition (e.g., of fat, carbohydrates, and proteins, and amounts of each). Determining the amount of insulin to inject at a given time can also require consideration of the effects of exercise and physiologic state. The patient's management of lifestyle factors such as body weight, diet, and exercise can significantly influence the type and effectiveness of therapy.

Management of diabetes involves large amounts of diagnostic data and prescriptive data that are acquired from medical devices, personal health care devices, patient recorded information, health care professional tests results, prescribed medications and recorded information. Medical devices including self-monitoring bG meters, continuous glucose monitors, insulin infusion pumps, diabetes analysis software, and diabetes device configuration software each of which generates or manages or both large amounts of diagnostic and prescriptive data. Personal health care devices can include weights, scales, blood pressure cuffs, pedometers, other activity monitors, and other suitable devices. Patient recorded data can include information relating to meals, exercise, and lifestyle. Health care professional biomarker data can include HbAlC, cholesterol, triglycerides, fasting glucose, and glucose tolerance. Health care professional recorded information can include therapy and other patient-specific information.

Data for executing one or more functions may be stored in nonvolatile memory of a medical device. When a function is to be executed, the data associated with the function may be loaded to volatile memory of the medical device and executed from the volatile memory. Thus, there is a need to verify that the data as loaded into the volatile memory of the medical device is the same as the data stored within the nonvolatile memory of the medical device.

The background description provided herein is for the purpose of generally presenting the context of the disclosure. Work of the presently named inventors, to the extent it is described in this background section, as well as aspects of the description that cannot otherwise qualify as prior art at the time of filing, are neither expressly nor impliedly admitted as prior art against the present disclosure.

SUMMARY

In one feature, a method of checking the integrity of a dynamic link library (DLL) file called by an application being executed on a handheld medical device is described. The method includes loading a DLL from a read only memory (ROM) to a random access memory (RAM) beginning at a fixed location in the RAM. The DLL includes a first routine for performing a safety critical function of the handheld medical device and includes a second routine for performing a cyclical redundancy check (CRC) for the DLL once the DLL is loaded to the RAM. The method further includes selectively executing the first routine from the RAM to perform the safety critical function. The method further includes selectively executing the second routine from the RAM to perform the CRC including: calculating a check value based on the DLL loaded to the RAM; comparing the check value with a predetermined check value set for the CRC; and generating an output indicating that an error is present when the check value is different than the predetermined check value.

In one feature, a method of checking the integrity of a shared file that is called by an application being executed on a handheld medical device and that is callable by one or more other applications that are executable on the handheld medical device is described. The method includes loading the file from nonvolatile memory to a volatile memory beginning at a fixed location in the volatile memory. The shared file includes a first routine for performing a function of the handheld medical device and a second routine for performing an error detection function on the shared file once the shared file is loaded to the volatile memory. The method further includes selectively executing the first routine from the volatile memory to perform the function. The method further includes selectively executing the second routine from the volatile memory including: selectively calculating an error detection value based on the shared file; comparing the error detection value with a predetermined value set for the error detection function; and generating an output indicating that an error is present when the error detection value is different than the predetermined value.

In one feature, a method of preparing a dynamic link library (dll) file for execution by an application on a handheld medical device, the application loading the DLL from a read only memory (ROM) of the handheld medical device to a random access memory (RAM) of the handheld device beginning at a fixed location of the RAM before execution is described. The method includes compiling, at a remote computer, the DLL based on code generated based on user input. The DLL includes a first routine for performing a safety critical function of the handheld medical device and includes a second routine for a performing a cyclical redundancy check (CRC) on identified portions of the DLL. The method further includes calculating, at the remote computer, a check value based on the identified portions of the DLL; and selectively setting, at the remote computer, a predetermined value in the DLL to the check value. Performance of the CRC using the handheld medical device includes calculating a second check value based on the identified portions of the DLL once the DLL is loaded to the RAM and comparing the second check value with the predetermined value.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIGS. 6A-6B include example memory maps of example dynamic link library (DLL) files;

DETAILED DESCRIPTION

Figure 1:
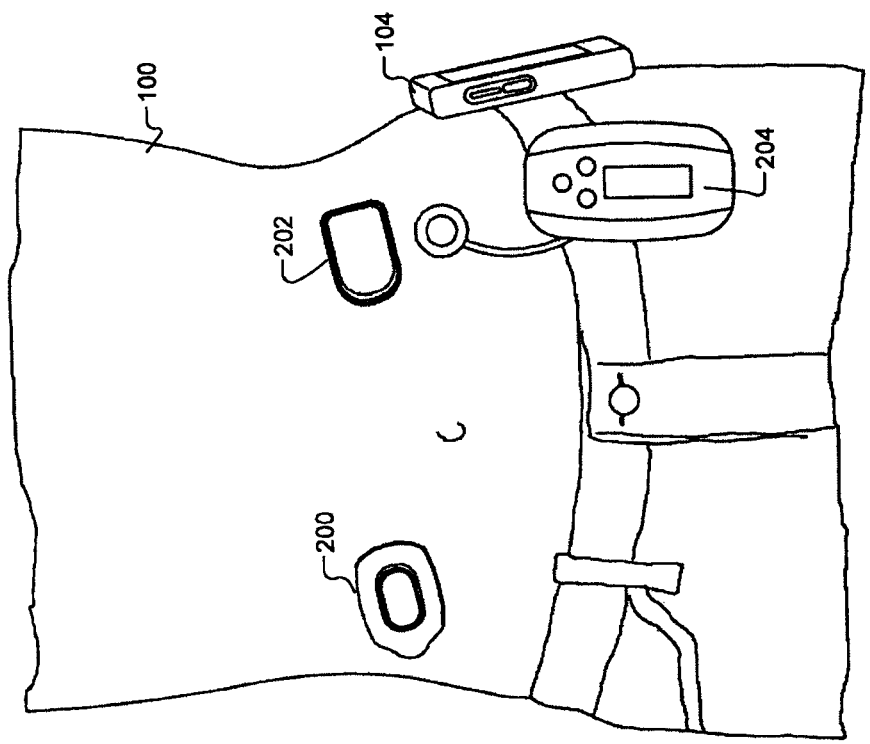
FIG. 1 shows a patient and a health care professional along with various devices that can be used to help the patient monitor and control health.

The following description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method can be executed in different order without altering the principles of the present disclosure.

Referring now to FIG. 1, a patient 100 with diabetes and a health care professional 102 are shown in a clinical environment. The patient 100 with diabetes can be diagnosed with a metabolic syndrome, pre-diabetes, type 1 diabetes, type 2 diabetes, gestational diabetes, etc. Healthcare providers for diabetes are diverse and include nurses, nurse practitioners, physicians, endocrinologists, and others and are collectively referred to as health care professionals.

During a health care consultation, the patient 100 typically shares with the health care professional 102 a variety of data including blood glucose (bG) measurements, continuous glucose monitor data, amounts and type of insulin administered, amounts of food and beverages consumed, exercise schedules, health status, and other lifestyle information. The health care professional 102 can obtain additional data for the patient 100, such as measurements of HbA1C, cholesterol levels, plasma glucose, triglycerides, blood pressure, and weight. The data can be recorded manually or electronically on a handheld diabetes management device 104 (e.g., a handheld bG monitor device), a diabetes analysis software executed on a personal computer (PC) 106, and/or a web-based diabetes analysis site. The health care professional 102 can analyze the patient data manually or electronically using the diabetes analysis software and/or the web-based diabetes analysis site. After analyzing the data and reviewing how efficacious previously prescribed therapy is and how well the patient 100 followed the previously prescribed therapy, the health care professional 102 can decide whether to modify a therapy prescribed for the patient 100.

Figure 2:
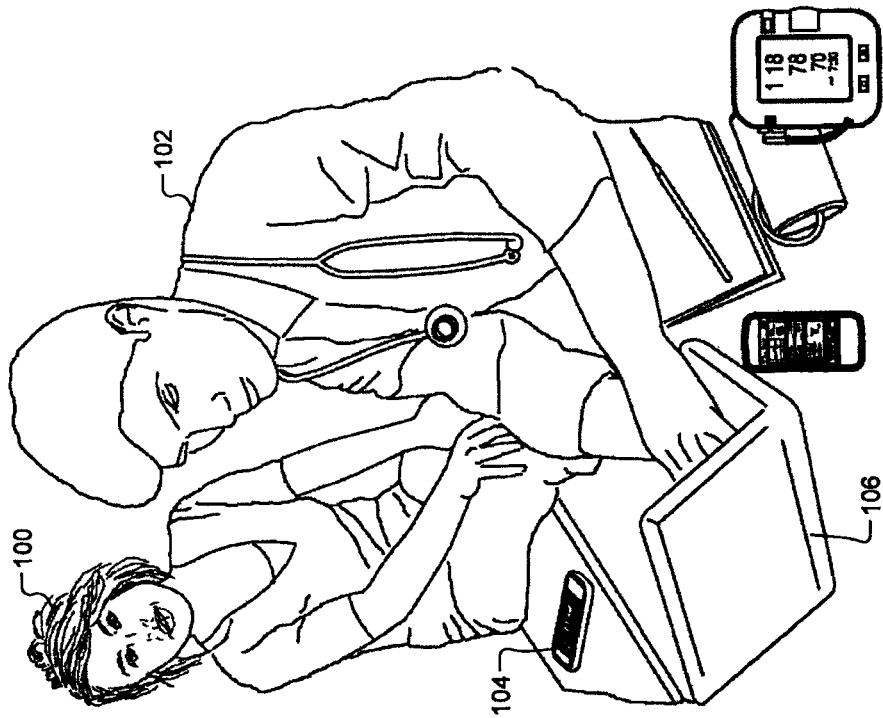
FIG. 2 shows a patient with a continuous glucose monitor (CGM), an ambulatory durable insulin infusion pump, an ambulatory non-durable insulin infusion pump, and a blood glucose (bG) management device.

Referring now to FIG. 2, the patient 100 can use a continuous glucose monitor (CGM) 200, an ambulatory durable insulin infusion pump 204 or an ambulatory non-durable insulin infusion pump 202 (collectively insulin pump 204), and the diabetes management device 104. The CGM 200 can use a subcutaneous sensor to sense and monitor the amount of glucose (e.g., glucose concentration) of the patient 100. The CGM 200 communicates glucose measurements to the diabetes management device 104.

The diabetes management device 104 performs various tasks including measuring and recording bG measurements, determining an amount of insulin to be administered to the patient 100 via the insulin pump 204, receiving user input via a user interface, archiving data, performing structured bG tests, etc. The diabetes management device 104 can transmit instructions to the insulin pump 204, and the insulin pump 204 selectively delivers insulin to the patient 100. Insulin can be delivered in the form of a meal bolus dose, a correction bolus dose, a basal dose, etc.

Figure 3:
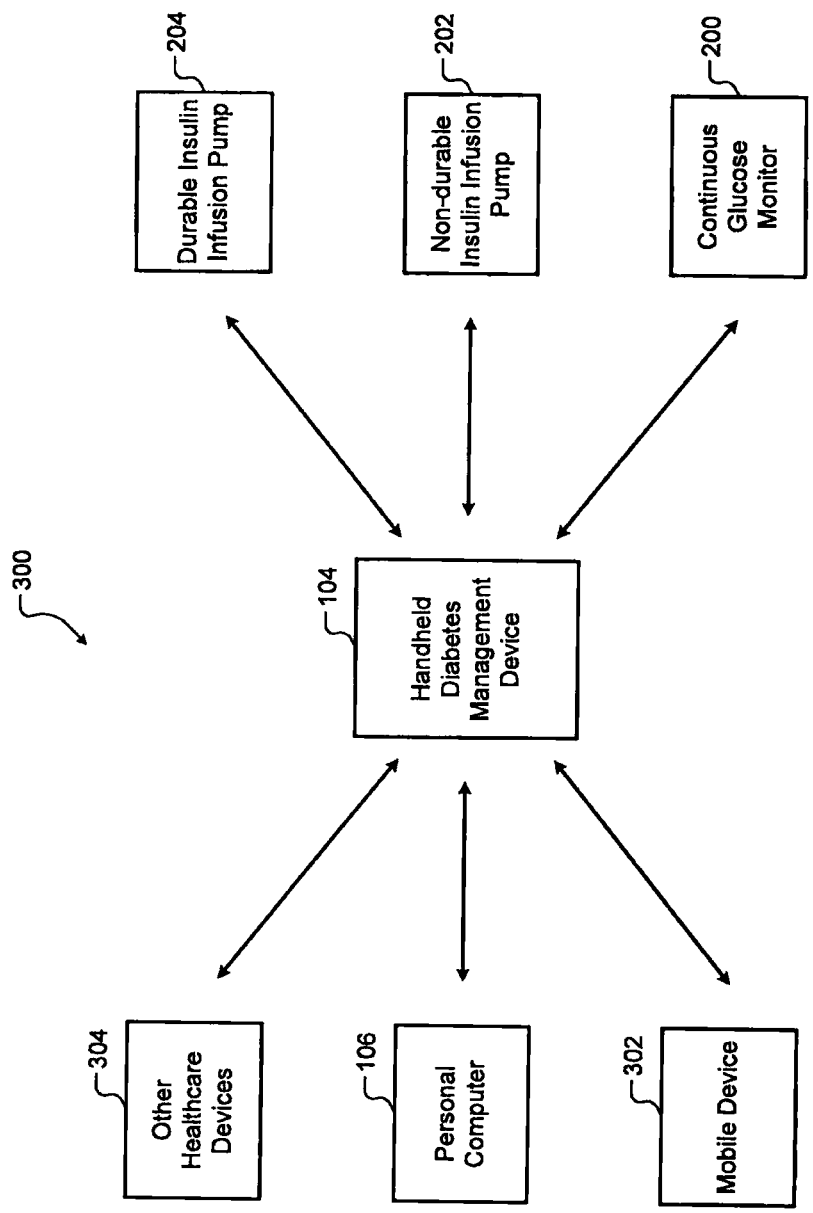
FIG. 3 shows a diabetes care system of systems that can be used to manage diabetes.

Referring now to FIG. 3, a diabetes management system 300 is shown which can be used by the patient 100 and/or the health care professional 102. The system 300 can include one or more of the following devices: the diabetes management device 104, the CGM 200, the insulin pump 204, a mobile device 302, the diabetes management software executed on the computer 106, and one or more other health care devices 304. The diabetes management device 104 can be configured as a system "hub" and communicate with one or more of the other devices of the system 300. The insulin pump 204, the mobile device 302, or another suitable device can alternatively serve as the system hub. Communication between various devices in the system 300 can be performed using wireless interfaces (e.g., Bluetooth) and/or wired interfaces (e.g., USB). Communication protocols used by these devices can include protocols compliant with the IEEE 11073 standard as extended using guidelines provided by Continua Health Alliance Design Guidelines. Further, health care records systems such as Microsoft Health Vault™ and Google Health™ can be used by the patient 100 and the health care professional 102 to exchange information.

The diabetes management software running on the computer 106 can include an analyzer-configurator that stores configuration information for devices of the system 300. For example only, the configurator has a database to store configuration information for the diabetes management device 104 and the other devices. A patient can interface the configurator through standard web based or computer graphical user interfaces (GUIs). The configurator selectively transmits patient-approved configurations to the devices of the system 300. The analyzer selectively retrieves data from the devices of the system 300, stores the data in a database, selectively analyzes the data, and outputs analysis results through standard web based or computer GUIs.

Figure 4:
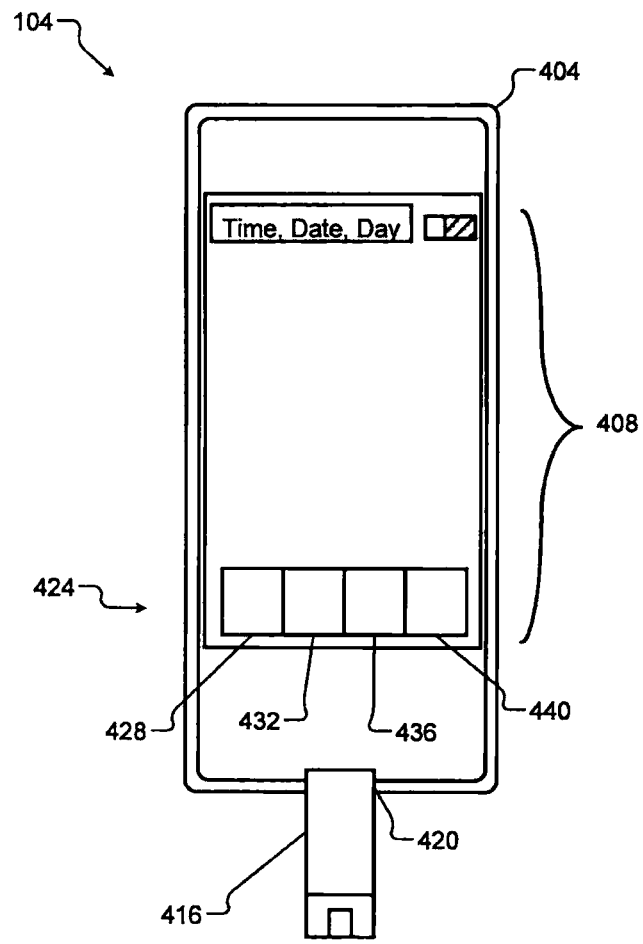
FIG. 4 is a high level diagram of an example implementation of a handheld diabetes management device.

Referring now to FIG. 4, a high level illustration of an example embodiment of the diabetes management device 104 is presented. The diabetes management device 104 includes, among other things, a housing 404, user unit control switches (not specifically numbered), a touchscreen display 408, and a bG test strip port 420. The user unit control switches, for example, can include ON/OFF switches, volume switches, alarm switches for bG testing and/or insulin administration, and/or one or more other switches or other types of control devices that a patient can use to control functions/operations of the diabetes management device 104.

A bG test strip 416 can be inserted into the bG test strip port 420. The bG test strip 416 can be inserted into the bG test strip port 420 by a patient, from a test strip drum (not shown) located within the housing 404, or in another suitable manner. The bG test strip 416 is shown already inserted into the bG test strip port 420 in the example of FIG. 4 and not yet inserted into the bG test strip port 420 in the example of FIG. 5A.

User selectable options 424 can be displayed on a portion of the display 408. The selectable options 424 can include a menu option 428, a bolus insulin option 432, a carbohydrate option 436, and an event option 440. One or more other user selectable options can additionally or alternatively be available. The patient can access a device menu for the diabetes management device 104 by selecting the menu option 428. The patient can input various insulin (and/or other medication) information (e.g., amount, insulin type, etc.) by selecting the bolus insulin option 432. The patient can input various carbohydrate intake information (e.g., amount) by selecting the carbohydrate option 436. The patient can also input other food intake information (e.g., protein content, fat content, etc.) by selecting the carbohydrate option 436. The patient can input various event related information (e.g., meals, exercise, periods of stress, etc.) that can affect the patient's bG measurements by selecting the event option 440.

Although the display 408 is described herein as a touch-screen display, the diabetes management device 104 can include another suitable form of display (e.g., LED, etc.). If a touchscreen display is not used, the user control switches can include specific buttons or controls by which the patient is able to select various options and input markers needed to operate the diabetes management device 104.

The above description is a broad description of the diabetes management device 104. In practice, the diabetes management device 104 can include additional controls, input ports, output ports, etc., as can be desired to further enhance its utility or its use with other components and devices (e.g., computers, infusion pumps, cellular phones, etc.). The description of the diabetes management device 104 should not be taken as limiting as to the construction of the diabetes management device 104 or as to the features and capabilities of the diabetes management device 104.

As used herein, the term "module" can refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term "module" can include memory (shared, dedicated, or group) that stores code executed by the processor.

The term "code," as used herein, can include software, firmware, and/or microcode, and can refer to programs, routines, functions, classes, and/or objects. The term "shared," as used above, means that some or all code from multiple modules can be executed using a single (shared) processor. In addition, some or all code from multiple modules can be stored by a single (shared) memory. The term "group," as used above, means that some or all code from a single module can be executed using a group of processors. In addition, some or all code from a single module can be stored using a group of memories.

The apparatuses and methods described herein can be implemented by one or more computer programs executed by one or more processors. The computer programs include processor-executable instructions that are stored on a non-transitory, tangible, computer readable medium. The computer programs can also include stored data. Examples of the non-transitory, tangible, computer readable medium include, but are not limited to, nonvolatile memory, magnetic storage, and optical storage.

Figure 5A:
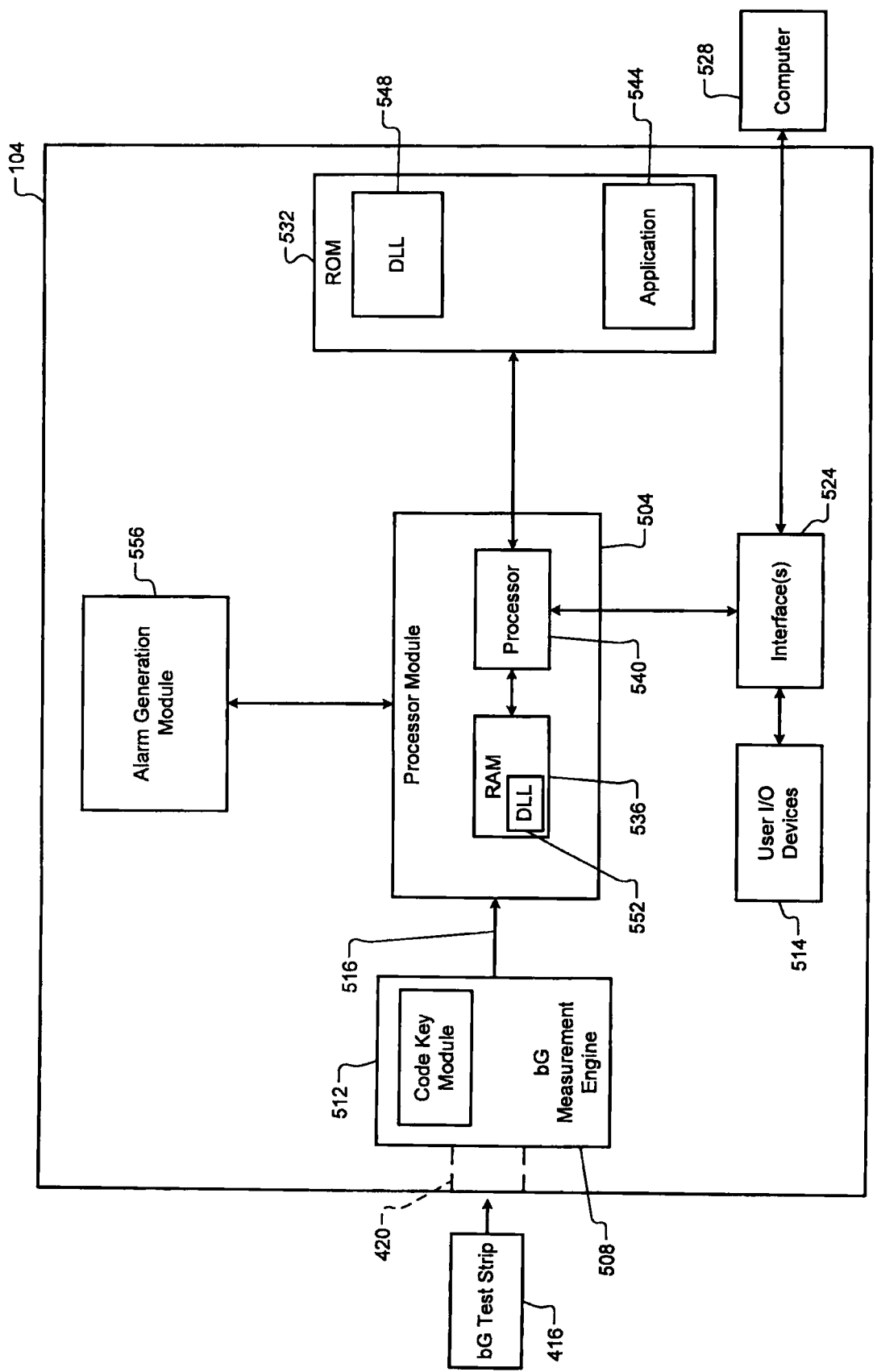
FIGS. 5A-5D include functional block diagrams of an example handheld diabetes management devices.
Figure 5B:
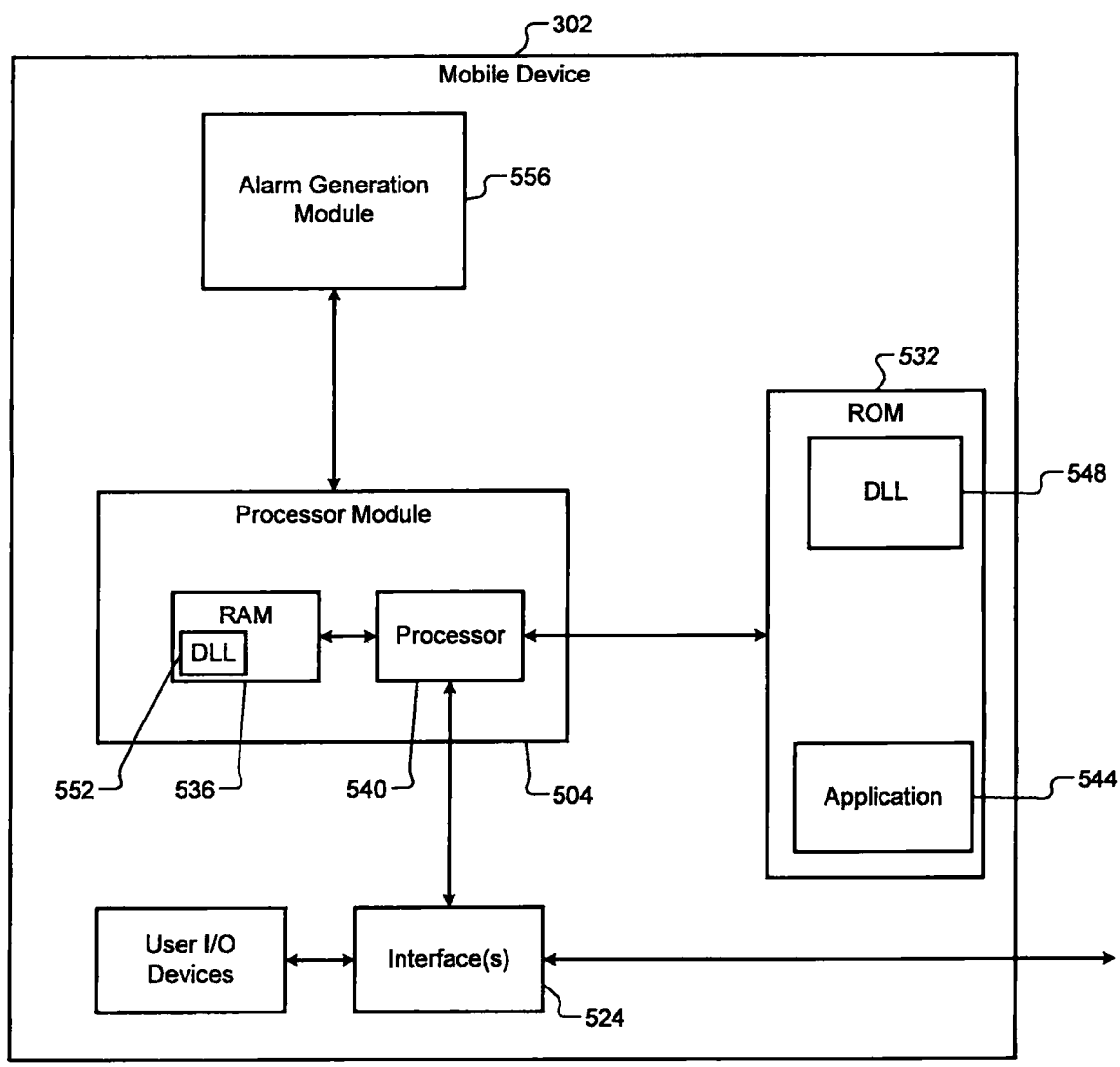
Figure 5C:
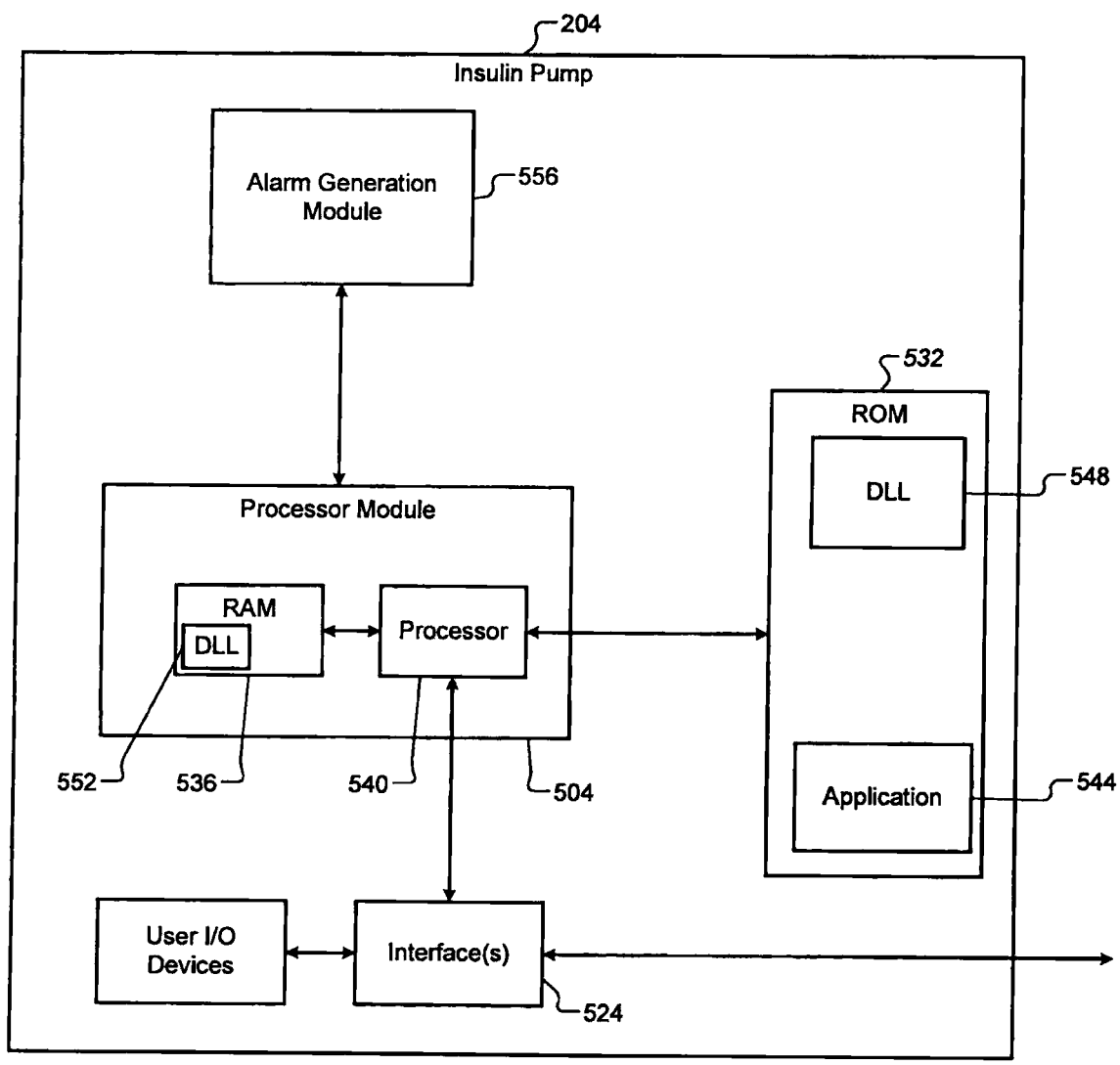
Figure 5D:
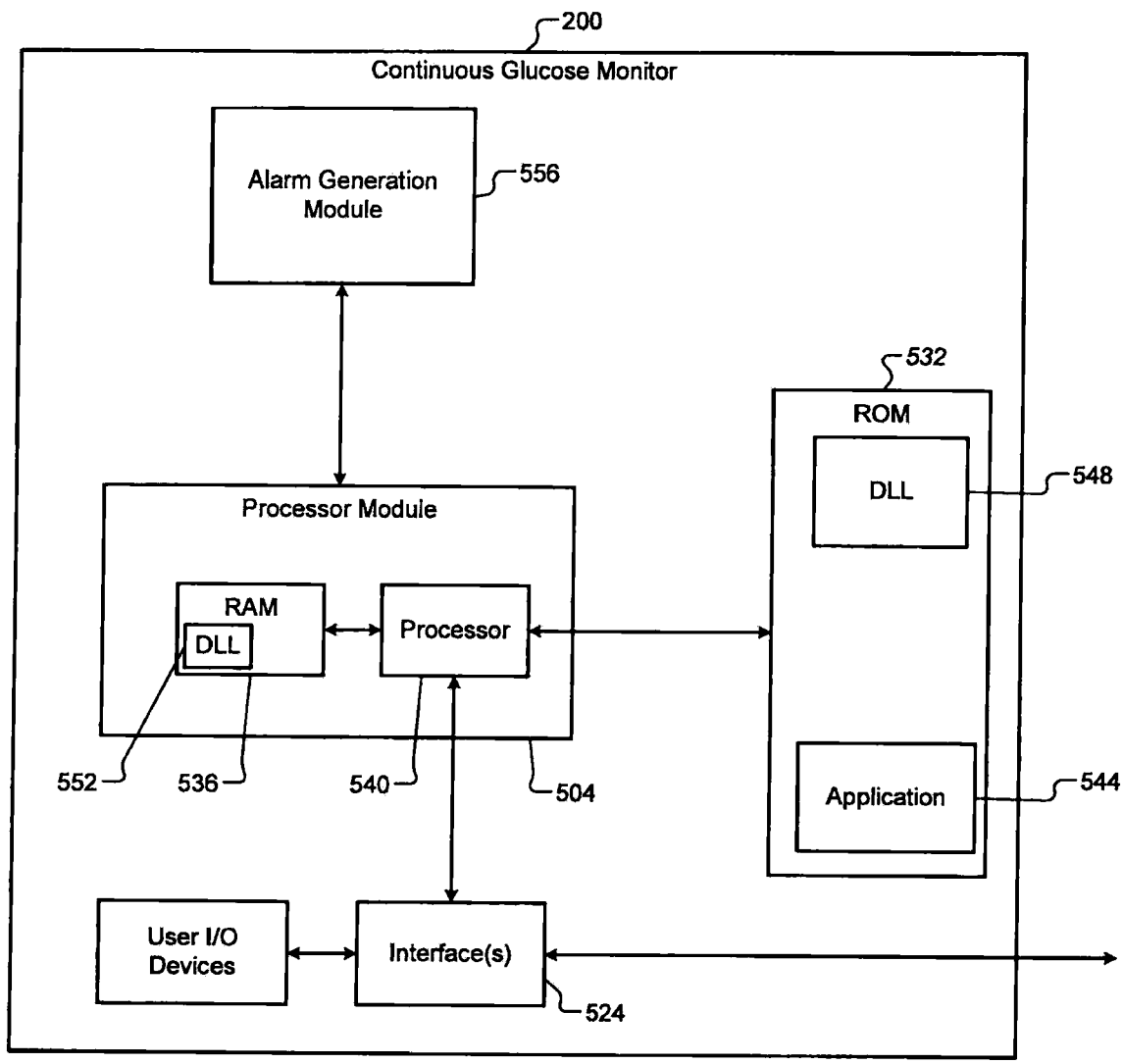

Referring now to FIG. 5A, a functional block diagram of an example implementation of the diabetes management device 104 is presented. While the present disclosure will be discussed in conjunction with the diabetes management device 104, the present disclosure is also applicable to other handheld medical devices, such as insulin pumps, CGMs, and other types of handheld medical devices, for example, as illustrated in the examples of FIGS. 5B-5D. The present disclosure is also applicable to non-medical devices.

The diabetes management device 104 includes a processor module (e.g., a microprocessor based subsystem) 504 that can receive information from a bG measurement engine 508. The bG measurement engine 508 can be located adjacent the bG test strip port 420. The bG measurement engine 508 reads (measures) a bG level of the bG test strip 416 inserted into the bG test strip port 420. The bG measurement engine 508 can include a code key module 512 that includes pre-calibrated data for determining a bG level from the bG test strip 416. The bG test strip 416 may be provided from the test strip drum housing unused bG test strips within the diabetes management device 104.

The bG measurement engine 508 generates bG sample data 516 based on its reading of the bG test strip 416. Among other things, the bG sample data 516 includes data indicative of the bG level of a blood sample on the bG test strip 416. The processor module 504 can also receive bG sample data from other sources, such as via the CGM 200, the display 408, and/or another suitable source.

The processor module 504 can receive user input data via one or more user input/output (I/O) devices 514, such as the display 408, one or more buttons/switches/etc., and/or one or more other user I/O devices. Data may be communicated between the processor module 504 and the user I/O devices 514 via one or more I/O interfaces 524. Data may also be communicated between the diabetes management device 104 and one or more other devices, such as a computer 528, via the I/O interface(s) 524. Data may be communicated between the diabetes management device 104 and one or more other devices wirelessly and/or by wire.

The diabetes management device 104 includes nonvolatile memory 532. The nonvolatile memory 532 may include a hard drive, one or more types of read only memory (ROM) (e.g., flash), and/or one or more other suitable types of nonvolatile memory. The diabetes management device 104 also includes volatile memory 536. The volatile memory 536 may include, for example, one or more types of random access memory (RAM) and/or one or more other suitable types of volatile memory. The volatile memory 536 may be implemented with a processor 540 within the processor module 504 or in another suitable location, such as external to the processor module 504.

An operating system manages operation of the diabetes management device 104. For example, the operating system may be the Windows CE operating system by Microsoft. One or more applications, such as an application 544 embodied as code stored in the nonvolatile memory 532, may be executed on the diabetes management device 104.

The application 544 (a calling application) may selectively call for execution of one or more safety critical functions and/or one or more other functions implemented within a shared file. For example, the application 544 may selectively call for execution of one or more safety critical functions and/or one or more other functions included within a dynamic link library (DLL) (file) 548, another shared library, or a shared object. Examples of safety critical functions in the context of diabetes/blood glucose management include advice regarding bolus insulin administration, advice regarding carbohydrate intake, and other safety critical functions. The present disclosure, however, is applicable to safety critical functions performed by handheld medical devices generally and is not limited to safety critical functions associated with diabetes/blood glucose management.

The application 544 may call for execution of a function included within the DLL 548 at predetermined time intervals, in response to the occurrence of one or more events, etc. The application 544 may issue an operating system function call (e.g., rundll) to call for execution of a function included within the DLL 548.

The function(s) within the DLL 548, however, are not executed from the nonvolatile memory 532. Instead, the processor 540 first loads the DLL 548 to the volatile memory 536, as illustrated by loaded DLL 552. One or more functions of the loaded DLL 552 can be executed from the loaded DLL 552 as the one or more functions are called by the application 544.

FIG. 6A includes an example memory map of an example DLL, such as the DLL 548. FIG. 6B includes another example memory map of an example DLL, such as the DLL 548. Referring now to FIG. 5A and FIGS. 6A-6B, the DLL 548 includes a fixed address (location) in the volatile memory 536 where the loading of the DLL 548 is to begin, as illustrated by 604. The loaded DLL 552 therefore begins at the fixed address. The DLL 548 also includes addresses where the other data within the DLL 548 should be loaded to the volatile memory 536 based on the loading beginning at the fixed location. For example only, the DLL 548 includes thirteen executable functions (Functions 1-13) collectively illustrated by 608. Each function has an address where (a beginning of) the function should be loaded to the volatile memory 536. For example, the first listed one of the functions 608, Function 1, should be loaded to address 50001000H of the volatile memory 536, the second listed one of the functions 608, Function 2, should be loaded to the address 50001078H, and so on.

One or more of the functions 608 are safety critical functions. Safety critical functions may refer to functions related to the safety of a user. One or more of the functions 608 are error detection functions, such as a 16-bit cyclical redundancy check (CRC) function, a 32-bit CRC function, a 64-bit CRC function, a checksum function, a hash function, or another suitable error detection function. For purposes of discussion only, the error detection function will be discussed as a CRC function. The application 544 may selectively execute the CRC function, such as before and after, only before, or only after execution of a safety critical function.

The DLL 548 also includes a DLL variable data section 612. While not shown in the example of FIG. 6A, the DLL variable data section may be located at 612. The data within the DLL variable data section changes as variables are populated and functions of the loaded DLL 552 are executed. As the data within the DLL variable data section of the loaded DLL 552 can change, the CRC function excludes the data within the DLL variable data section of the loaded DLL 552 when performing the CRC function.

The CRC function may identify the DLL variable data section of the loaded DLL 552 (for exclusion from the performance of the CRC function) using one or more identifiers that identify the boundaries between which the CRC function should be performed and the boundaries of the DLL variable data section. For example a first macro may utilize and identify the address of the first one of the functions 608. In the examples of FIGS. 6A and 6B, the address of the first one of the functions is 50001000H.

In the example of FIG. 6A, a second macro may utilize the address where the DLL variable data section begins. In the example of FIG. 6A, the address where the DLL variable data section begins is 50006040H. In the example of FIG. 6A, a third macro may utilize the address where the DLL variable data section ends. In the example of FIG. 6A, the address where the DLL variable data section ends is 5008E74H. In the example of FIG. 6A, the CRC function may calculate a check value based on: (i) the data between the first one of the functions 608 and the beginning of the DLL variable data section; and (ii) the data between the end of the DLL variable data section and the end of the loaded DLL 552. While the CRC function may calculate the check value based on the data stored in two different sections, the data may be stored in one section (as in the example of FIG. 6B) or in more than two different sections. For example, in the example of FIG. 6B, the data is stored in one section, and the CRC function may calculate the check value based on the data between the first one of the functions 608 and CRC data.

The DLL 548 also includes CRC data, which is illustrated at 616. The CRC data includes a predetermined (check) value illustrated at 616. Performance of the CRC function based on the loaded DLL 552 generates a value that can be compared with the predetermined value to determine whether the loaded DLL 552 includes one or more errors. The CRC data may be loaded at the end of the executable code and the constant/read only data that is used during execution of the loaded DLL 552. In the example of FIG. 6B, the CRC data may be located before the DLL variable data section. The CRC data including the predetermined value provides an identifiable boundary for performing the CRC function.

Execution of the CRC function includes calculating a check value based on the non-excluded data of the loaded DLL 552, determining the predetermined value, and comparing the calculated check value with the predetermined value. Execution of the CRC function may also include indicating a status of the CRC function, such as whether the CRC function passed or failed. The status may be set to fail when the check value is different than the predetermined value. The status may be set to pass when the check value is the same as the predetermined value.

The application 544 may execute one or more remedial actions when the CRC function failed. For example only, the application 544 may display an error message on the display 408 when the CRC function failed. The application 544 may additionally or alternatively set a predetermined indicator (e.g., message, code, flag, etc.) in a portion of the nonvolatile memory 532 that indicates that the CRC function associated with the safety critical function when the CRC function failed. For another example only, the application 544 may prompt an alarm generation module 556 to generate one or more tactile alarms, such as a sound, a light, a vibration, etc. when the CRC function failed. For another example only, the application 544 may refrain from outputting a result of the performance of the safety critical function when the CRC function failed. The code of the application 544 may be determinative of how the application 544 responds to a failure of the CRC function.

Figure 7:
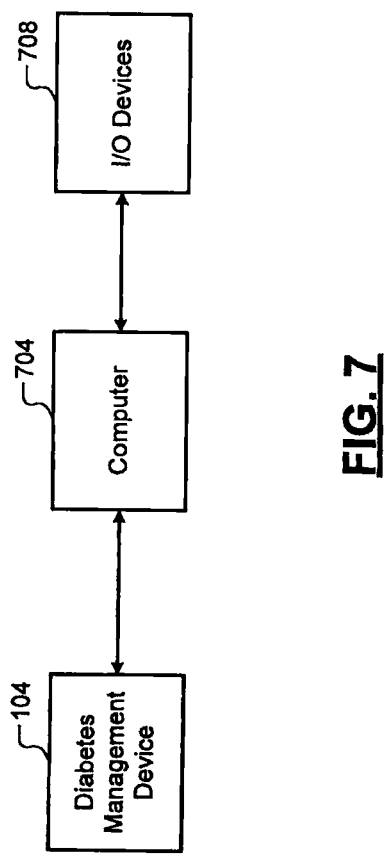
FIG. 7 includes a functional block diagram of an example DLL creation system.

Referring now to FIG. 7, a functional block diagram of an example DLL creation system is presented. Before the DLL 548 is stored in the nonvolatile memory 532, the DLL 548 may initially be built using a remote device, such as a computer 704. A user of the computer 704 may build the DLL 548 using, for example, a source code editor and compiler application and one or more I/O devices 708, such as a keyboard, a mouse, a display, etc.

Once the functions have been successfully built and coded into the DLL 548 on the computer 528, a testing application may be executed using the computer 704. A testing application may load the DLL 548 to volatile memory of the computer 704 and calculate the check value using the CRC function. The testing application may generate an output to the user of the computer 704 that is indicative of the check value. Via the source code editor and compiler application, the user of the computer 704 can update the predetermined value of the CRC data based on the check value. For example, ideally, the user will set the predetermined value equal to the check value. The DLL 548 can then be compiled, and the DLL 548 can later be stored within the nonvolatile memory 532 of the diabetes management device 104 using the computer 704 or another device. The DLL 548 can also be stored within nonvolatile memory of one or more other handheld medical devices that selectively call for execution of a safety critical function implemented within the DLL 548.

Figure 8:
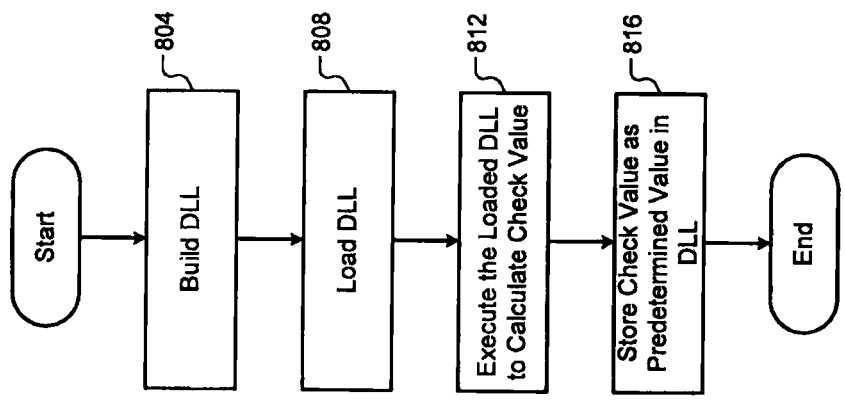
FIG. 8 includes a flowchart depicting an example method of creating and storing a DLL to a handheld medical device.

FIG. 8 is a flowchart depicting an example method that may be performed by the computer 704. Control may begin with 804 where control may build the DLL 548 for later storage in nonvolatile memory of one or more handheld medical devices, such as the diabetes management device 104. Control may build the DLL 548 using the source code editor and compiler application. Control loads the DLL 548 to volatile memory of the computer 704 at 808 for determining the check value.

At 812, control calculates the check value of the DLL loaded to the volatile memory of the computer 704 using the CRC function within DLL. Control may display the check value for a user of the computer 704. Control may also receive input from the user indicative of the check value. Control stores (or inputs) the check value in the CRC data (source code) of the DLL 548 for use during execution of a safety critical function and the CRC function on a handheld medical device at 816. Control may store the check value using the source code editor and compiler application. Control may also compile the DLL 548 at 816.

Figure 9:
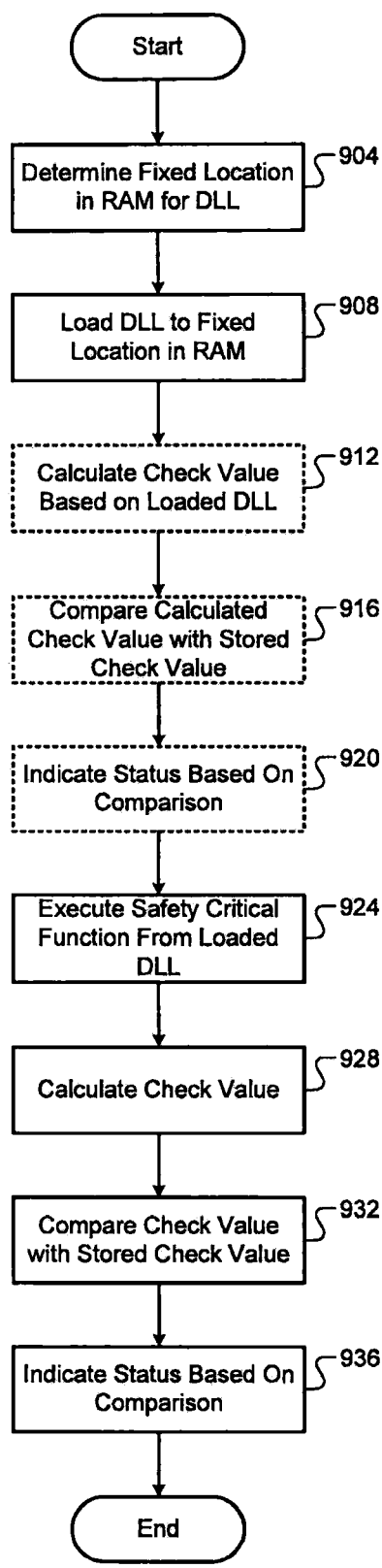
FIG. 9 includes a flowchart depicting an example method of executing a safety critical function using a handheld medical device.

Referring now to FIG. 9, a flowchart depicting an example method that may be performed by the application 544 for executing a safety critical function implemented within the DLL 548 is presented. Control may begin with 904 where control determines the fixed location in the volatile memory 536 specified in the DLL 548 starting at which the DLL 548 is to be loaded. At 908, control loads the DLL 548 to the volatile memory 536 beginning at the fixed location, thereby creating the loaded DLL 552. Once loaded to the volatile memory 536, one or more functions implemented within the loaded DLL 552 may be called and executed by the application 544.

In various implementations, control may execute the CRC function at 912-920 before executing the safety critical function from the loaded DLL 552 at 924. At 912, control may calculate the check value based on the loaded DLL 552, excluding the DLL variable data section of the loaded DLL 552. If variable data was used in calculating the check value, the check value may change as the variable data changed. The CRC data including the predetermined value stored within the loaded DLL 552 is also excluded from the calculation of the check value.

At 916, control may compare the calculated check value with the predetermined value stored within the loaded DLL 552. Control may indicate the status of the performance of the CRC function at 920. Control may indicate that the CRC function failed when the check value is different than the predetermined value. Control may indicate that the CRC function passed when the check value is equal to the predetermined value.

At 924, control executes the safety critical function from the loaded DLL 552. Control executes the CRC function at 928-936. A more detailed example method of executing the CRC function is illustrated in FIG. 10, which is discussed further below. At 928, control calculates the check value based on the loaded DLL 552, excluding the DLL variable data section of the loaded DLL 552. The CRC data including the predetermined value stored within the loaded DLL 552 is also excluded from the calculation of the check value.

At 932, control compares the calculated check value with the predetermined value stored within the loaded DLL 552. Control may indicate the status of the performance of the CRC function at 936. Control may indicate that the CRC function failed when the check value is different than the predetermined value. Control may indicate that the CRC function passed when the check value is equal to the predetermined value. Control may take one or more remedial actions when the CRC function failed. For example only, control may display an indicator that an error is present, refrain from displaying a result of the safety critical function, and/or perform one or more other suitable remedial actions.

Figure 10A:
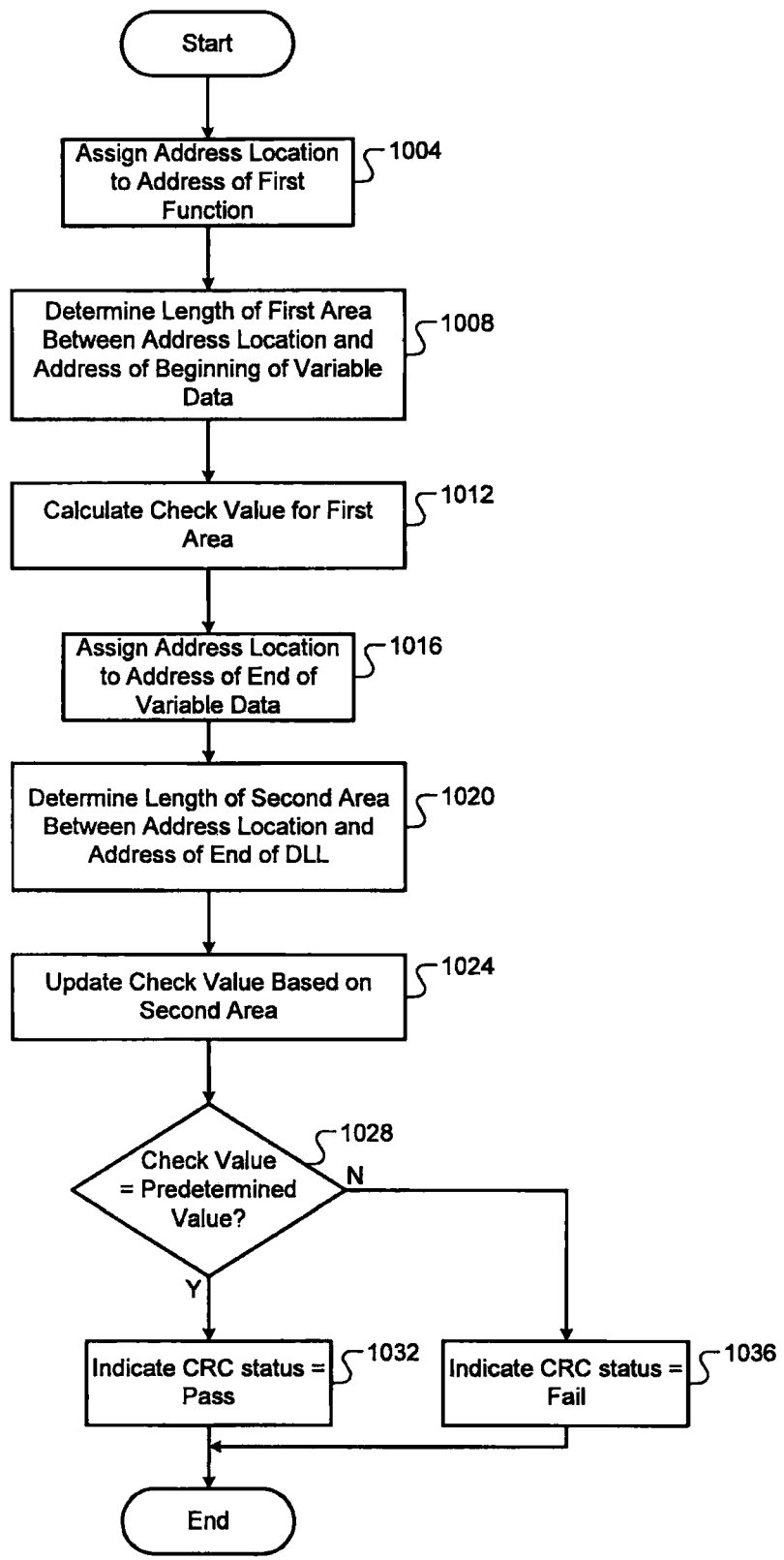
FIGS. 10A-10B include flowcharts depicting example methods of executing a cyclical redundancy check (CRC).

Referring now to FIG. 10A, a flowchart depicting an example method of executing the CRC function that may be performed by the application 544 is presented. As in the example of FIG. 10A, the loaded DLL 552 may include two areas (first and second areas) based upon which the check value can be calculated. The two areas may be separated by the DLL variable data section.

Control may begin with 1004 where control assigns an address location to the address of the first function within the loaded DLL 552. At 1008, control determines the length of a first area of the loaded DLL 552 that is between the assigned address location (i.e., the address of the first function) and the address of the beginning of the DLL variable data section of the loaded DLL 552. Control calculates the check value for the first area of the loaded DLL 552 at 1012.

At 1016, control assigns the address location to the end of the DLL variable data section of the loaded DLL 552. Control determines the length of a second area of the loaded DLL 552 that is between the assigned address location (i.e., the address of the end of the DLL variable data section) and the end of the loaded DLL 552 at 1020. At 1024, control updates the check value based on the second area of the loaded DLL 552. Control determines the predetermined value and determines whether the check value is equal to the predetermined value at 1028. If true, control indicates that the CRC function passed at 1032. If false, control indicates that the CRC function failed at 1036. Control may take one or more remedial actions when the CRC function failed. For example only, control may display an indicator that an error is present, refrain from displaying a result of the safety critical function, and/or perform one or more other suitable remedial actions.

Figure 10B:
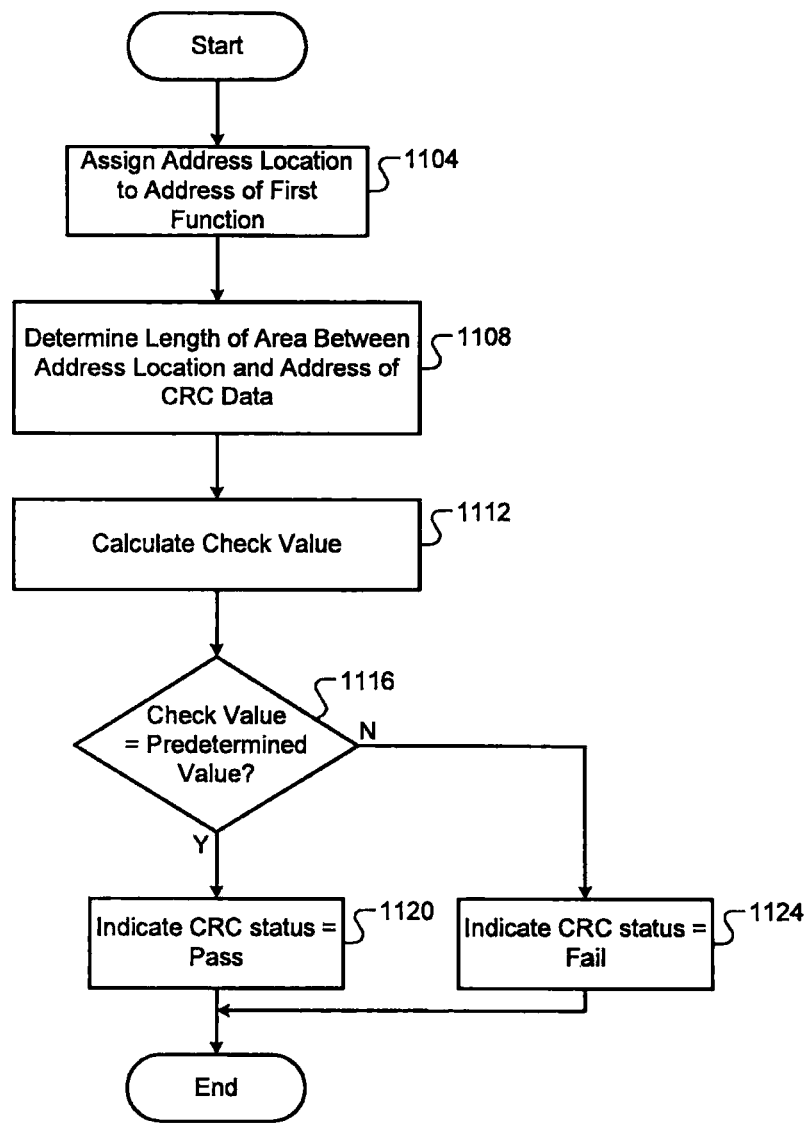

Referring now to FIG. 10B, a flowchart depicting an example method of executing the CRC function that may be performed by the application 544 is presented. As in the example of FIG. 10B, the loaded DLL 552 may include one area based upon which the check value can be calculated, and the DLL variable data section may be located after the CRC data.

Control may begin with 1104 where control assigns an address location to the address of the first function within the loaded DLL 552. At 1108, control determines the length of the loaded DLL 552 that is between the assigned address location (i.e., the address of the first function) and the address of the CRC data. Control calculates the check value for the area of the loaded DLL 552 at 1112.

Control determines the predetermined value and determines whether the check value is equal to the predetermined value at 1116. If true, control indicates that the CRC function passed at 1120. If false, control indicates that the CRC function failed at 1124. Control may take one or more remedial actions when the CRC function failed. For example only, control may display an indicator that an error is present, refrain from displaying a result of the safety critical function, and/or perform one or more other suitable remedial actions.

In a feature, a method of checking the integrity of a dynamic link library (DLL) file called by an application being executed on a handheld medical device is described. The method includes loading a DLL from a read only memory (ROM) to a random access memory (RAM) beginning at a fixed location in the RAM. The DLL includes a first routine for performing a safety critical function of the handheld medical device and includes a second routine for performing a cyclical redundancy check (CRC) for the DLL once the DLL is loaded to the RAM. The method further includes selectively executing the first routine from the RAM to perform the safety critical function. The method further includes selectively executing the second routine from the RAM to perform the CRC including: calculating a check value based on the DLL loaded to the RAM; comparing the check value with a predetermined check value set for the CRC; and generating an output indicating that an error is present when the check value is different than the predetermined check value.

In other features, the CRC is a 32-bit CRC.

In still other features, the method further comprises generating the output indicating that the error is not present when the check value is equal to the predetermined check value.

In further features, the method further comprises selectively taking a remedial action based on whether the output indicates that the error is present.

In still further features, the method further comprises, when the output indicates that the error is present, displaying an indicator of the error on a display of the handheld medical device.

In other features, the safety critical function includes calculating and displaying a suggested amount for a bolus administration of insulin.

In still other features, the method further comprises determining the fixed location in the RAM at which a beginning of the DLL is to be loaded.

In further features, the method further comprises excluding, from the performance of the CRC, one or more portions of the DLL where changeable data is stored. The changeable data is selectively changed during execution of one or more routines included within the DLL.

In still further features, the method further comprises: determining a first beginning point and a first ending point of the DLL; determining a second beginning point and a second ending point of the DLL; and performing the CRC based on: (i) a first portion of the DLL between the first beginning and ending points; and (ii) a second portion of the DLL between the second beginning and ending points. The first beginning and ending points and the second beginning and ending points are different from each other.

In other features, the method further comprises: determining a first location of a first function of the DLL; determining a second location of CRC data of the DLL function; and performing the CRC based on a portion of the DLL between the first and second locations.

In other features, the handheld medical device is one of a handheld diabetes management device, a continuous blood glucose (bG) monitor, and an insulin pump.

In another feature, a method of checking the integrity of a shared file that is called by an application being executed on a handheld medical device and that is callable by one or more other applications that are executable on the handheld medical device is described. The method includes loading the file from nonvolatile memory to a volatile memory beginning at a fixed location in the volatile memory. The shared file includes a first routine for performing a function of the handheld medical device and a second routine for performing an error detection function on the shared file once the shared file is loaded to the volatile memory. The method further includes selectively executing the first routine from the volatile memory to perform the function. The method further includes selectively executing the second routine from the volatile memory including: selectively calculating an error detection value based on the shared file; comparing the error detection value with a predetermined value set for the error detection function; and generating an output indicating that an error is present when the error detection value is different than the predetermined value.

In other features, the error detection function is a 32-bit cyclical redundancy check (CRC).

In still other features, the method further comprises generating the output indicating that the error is not present when the error detection value is equal to the predetermined value.

In further features, the method further includes selectively taking a remedial action based on whether the error is present.

In still further features, the method further includes, when the output indicates that the error is present, displaying an indicator of the error on a display of the handheld medical device.

In other features, the function includes displaying a suggested amount for a bolus administration of insulin.

In still other features, the method further includes excluding, from the performance of the error detection function, one or more portions of the shared file where changeable data is stored. The changeable data is selectively changed during execution of one or more routines included within the shared file.

In further features, the method further comprises: determining a first beginning point and a first ending point of the shared file; determining a second beginning point and a second ending point of the shared file; and performing the error detection function based on: (i) a first portion of the shared file between the first beginning and ending points; and (ii) a second portion of the shared file between the second beginning and ending points. The first beginning and ending points and the second beginning and ending points are different from each other.

In further features, the method further comprises: determining a first location of a first function of the shared file; determining a second location of CRC data of the shared file; and performing the error detection function based on a portion of the shared file between the first and second locations.

In still further features, shared file is a dynamic link library (DLL).

In other features, the handheld medical device is one of a handheld diabetes management device, a continuous blood glucose (bG) monitor, and an insulin pump.

In another feature, a method of preparing a dynamic link library (dll) file for execution by an application on a handheld medical device, the application loading the DLL from a read only memory (ROM) of the handheld medical device to a random access memory (RAM) of the handheld device beginning at a fixed location of the RAM before execution is described. The method includes compiling, at a remote computer, the DLL based on code generated based on user input. The DLL includes a first routine for performing a safety critical function of the handheld medical device and includes a second routine for a performing a cyclical redundancy check (CRC) on identified portions of the DLL. The method further includes calculating, at the remote computer, a check value based on the identified portions of the DLL; and selectively setting, at the remote computer, a predetermined value in the DLL to the check value. Performance of the CRC using the handheld medical device includes calculating a second check value based on the identified portions of the DLL once the DLL is loaded to the RAM and comparing the second check value with the predetermined value.

In other features, the method further comprises: generating, at the remote computer, an output indicative of the check value for display to a user in response to the output; and receiving, at the remote computer, input indicative of the check value input by a user.

The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

What is claimed is:

1. A method of checking the integrity of a dynamic link library (DLL) file called by an application being executed on a handheld medical device, the method comprising:
    loading a DLL from nonvolatile memory to volatile memory beginning at a fixed location in the volatile memory,
    the DLL including a first routine for performing a safety critical function of the handheld medical device and including a second routine for performing a cyclical redundancy check (CRC) for the DLL once the DLL is loaded to the volatile memory;
    selectively executing the first routine from the volatile memory to perform the safety critical function;
    selectively executing the second routine from the volatile memory to perform the CRC including:
        calculating a check value based on the DLL loaded to the volatile memory;
        comparing the check value with a predetermined check value set for the CRC; and
        generating an output indicating that an error is present when the check value is different than the predetermined check value.

2. The method of claim 1 wherein the CRC is a 32-bit CRC.

3. The method of claim 1 further comprising generating the output indicating that the error is not present when the check value is equal to the predetermined check value.

4. The method of claim 3 further comprising selectively taking a remedial action based on whether the output indicates that the error is present.

5. The method of claim 4 further comprising, when the output indicates that the error is present, displaying an indicator of the error on a display of the handheld medical device.

6. The method of claim 1 wherein the safety critical function includes calculating and displaying a suggested amount for a bolus administration of insulin.

7. The method of claim 1 further comprising determining the fixed location in the volatile memory at which a beginning of the DLL is to be loaded.

8. The method of claim 1 further comprising excluding, from the performance of the CRC, one or more portions of the DLL where changeable data is stored,
    wherein the changeable data is selectively changed during execution of one or more routines included within the DLL.

9. The method of claim 1 further comprising:
    determining a first beginning point and a first ending point of the DLL;
    determining a second beginning point and a second ending point of the DLL; and
    performing the CRC based on:
        (i) a first portion of the DLL between the first beginning and ending points; and
        (ii) a second portion of the DLL between the second beginning and ending points,
    wherein the first beginning and ending points and the second beginning and ending points are different from each other.

10. The method of claim 1 further comprising:
    determining a first location of a first function of the DLL;
    determining a second location of CRC data of the DLL function; and
    performing the CRC based on a portion of the DLL between the first and second locations.

11. The method of claim 1 wherein the handheld medical device is one of a handheld diabetes management device, a continuous blood glucose (bG) monitor, and an insulin pump.

12. A method of checking the integrity of a shared library file that is called by an application being executed on a handheld medical device and that is callable by one or more other applications that are executable on the handheld medical device, the method comprising:
when called for during execution of the application, loading the shared library file from nonvolatile memory to a volatile memory beginning at a fixed location in the volatile memory,
the shared library file is an executable file that includes a first routine for performing a function of the handheld medical device and including a second routine for performing a cyclical redundancy check (CRC) for the shared library file once the shared library file is loaded to the volatile memory;
when called for during execution of the application, selectively executing the first routine of the shared library file from the volatile memory to perform the function;
when called for during execution of the application, selectively executing the second routine of the shared library file from the volatile memory including:
selectively calculating a check value based on the shared library file;
comparing the check value with a predetermined value set for the CRC; and
generating an output indicating that an error is present when the check value is different than the predetermined value.

13. The method of claim 12 wherein the CRC is a 32-bit cyclical redundancy check (CRC).

14. The method of claim 12 further comprising generating the output indicating that the error is not present when the check value is equal to the predetermined value.

15. The method of claim 14 further comprising selectively taking a remedial action based on whether the error is present.

16. The method of claim 15 further comprising, when the output indicates that the error is present, displaying an indicator of the error on a display of the handheld medical device.

17. The method of claim 12 wherein the function includes displaying a suggested amount for a bolus administration of insulin.

18. The method of claim 12 further comprising excluding, from the performance of the CRC, one or more portions of the shared library file where changeable data is stored,
wherein the changeable data is selectively changed during execution of one or more routines included within the shared library file.

19. The method of claim 12 further comprising:
determining a first beginning point and a first ending point of the shared library file;
determining a second beginning point and a second ending point of the shared library file; and
performing the CRC based on:
(i) a first portion of the shared library file between the first beginning and ending points; and
(ii) a second portion of the shared library file between the second beginning and ending points,
wherein the first beginning and ending points and the second beginning and ending points are different from each other.

20. The method of claim 12 further comprising:
determining a first location of a first function of the shared library file;
determining a second location of CRC data of the shared library file; and
performing the CRC based on a portion of the shared library file between the first and second locations.

21. The method of claim 12 wherein the handheld medical device is one of a handheld diabetes management device, a continuous blood glucose (bG) monitor, and an insulin pump.

22. A method of preparing a dynamic link library (DLL) file for execution by an application on a handheld medical device, the application loading the DLL from nonvolatile memory of the handheld medical device to volatile memory of the handheld device beginning at a fixed location of the volatile memory before execution, the method comprising:
compiling, at a remote computer, the DLL based on code generated based on user input,
the DLL including a first routine for performing a safety critical function of the handheld medical device and including a second routine for a performing a cyclical redundancy check (CRC) on identified portions of the DLL;
calculating, at the remote computer, a check value based on the identified portions of the DLL; and
selectively setting, at the remote computer, a predetermined value in the DLL to the check value,
wherein the performance of the CRC using the handheld medical device includes calculating a second check value based on the identified portions of the DLL once the DLL is loaded to the volatile memory and comparing the second check value with the predetermined value.

23. The method of claim 22 further comprising:
generating, at the remote computer, an output indicative of the check value for display to a user in response to the output; and
receiving, at the remote computer, input indicative of the check value input by a user.

24. The method of claim 23 further comprising:
generating, at the remote computer, an output indicative of the check value for display to a user in response to the output; and
receiving, at the remote computer, input indicative of the check value input by a user.

25. A method of preparing a shared library file for execution by an application on a handheld medical device, the application loading the shared library file from non-volatile memory of the handheld medical device to volatile memory of the handheld device beginning at a fixed location of the volatile memory before execution, the method comprising:
compiling, at a remote computer, the shared library file based on code generated based on user input,
the shared library file including a first routine for performing a safety critical function of the handheld medical device and including a second routine for performing a cyclical redundancy check (CRC) on identified portions of the shared library file;
calculating, at the remote computer, a check value based on the identified portions of the shared library file; and
selectively setting, at the remote computer, a predetermined value in the shared library file to the check value,
wherein the performance of the CRC using the handheld medical device includes calculating a second check value based on the identified portions of the shared library file once the shared library file is loaded to the volatile memory and comparing the second check value with the predetermined value.

* * * * *